United States Patent [19]

Muller

[11] 4,093,638

[45] June 6, 1978

[54] SIMULTANEOUS PREPARATION OF ORGANIC ACID CHLORIDES AND TRICHLOROACRYLOYL CHLORIDE AND PRODUCT

[75] Inventor: Francois Muller, Saint-Auban, France

[73] Assignee: Produits Chimiques Pechiney-Saint-Gobain, France

[21] Appl. No.: 454,114

[22] Filed: Mar. 25, 1974

Related U.S. Application Data

[63] Continuation of Ser. No. 764,944, Oct. 3, 1968, abandoned.

[30] Foreign Application Priority Data

Oct. 23, 1967    France ............................. 67.125439

[51] Int. Cl.$^2$ ............................. C09F 7/00; C11C 3/00

[52] U.S. Cl. ............................. 260/408; 260/544 R; 260/544 L; 260/544 D; 260/544 Y

[58] Field of Search ............... 260/408, 544 R, 544 L, 260/544 D, 544 Y

[56] References Cited

U.S. PATENT DOCUMENTS

| | | | |
|---|---|---|---|
| 1,921,767 | 8/1933 | Mills | 260/544 |
| 3,234,274 | 2/1966 | Renekhoff | 260/544 |
| 3,449,416 | 6/1969 | Brotherton | 260/544 |
| 3,829,477 | 8/1974 | Strini | 260/544 |

*Primary Examiner*—Winston A. Douglas
*Assistant Examiner*—John F. Niebling

[57] ABSTRACT

The preparation of organic acid chlorides and trichloroacryloyl chloride simultaneously by reaction of hexachloropropene with an organic acid.

17 Claims, No Drawings

SIMULTANEOUS PREPARATION OF ORGANIC ACID CHLORIDES AND TRICHLOROACRYLOYL CHLORIDE AND PRODUCT

This is a continuation, of application Ser. No. 764,944, filed Oct. 3, 1968 now abandoned.

The present invention relates to organic acid chlorides and trichloroacryloyl chloride and the process for simultaneous preparation from hexachloropropene.

It is known to manufacture organic acid chlorides from their corresponding acids by using reactants such as oxalylchloride, phosphorus pentachloride and thionyl chloride. Such procedures have the disadvantage of being particularly burdensome. It is also known to manufacture acid chlorides by chlorination of corresponding acids with materials, such as phosgene, but which have to be used with caution. It is likewise known to manufacture acid chlorides by reaction of phosphorus trichloride on the corresponding acids. Before the final step of distilling the acid chlorides, the aforementioned procedure necessitates intermediate steps, such as decanting the phosphoric acid which has been formed.

It is an object of this invention to provide a simple and efficient process for the preparation of acid chlorides by reaction of the corresponding organic acids with hexachloropropene and in which the process is accompanied by the formation of trichloroacryloyl chloride which has valuable properties.

The object of this invention of simultaneous preparation of organic acid chlorides and trichloroacryloyl chloride consists in mixing hexachloropropene and organic acids having the general formula

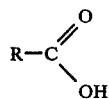

in which R represents a group such as hydrogen, alkyl, alkenyl, alkynyl, aryl, cycloalkane, cycloalkene or heterocyclic group, in which the organic group may be substituted or unsubstituted. The reaction is carried out in the absence or in the presence of catalysts, such as zinc chloride, ferric chloride or iodine, followed by heating said mixture to a temperature within the range of 50° to 220° C and preferably within the range of 120° to 180° C, and then distilling the reaction mixture to separate the trichloroacryloyl chloride and the organic acid chlorides which have been formed.

The step of mixing hexachloropropene and the organic acids can be carried out by simultaneous introduction of hexachloropropene and said organic acids into the reaction zone. However, it is desirable to carry out the mixing operation by first introducing the organic acid into the reaction zone, followed by the hexachloropropene, especially when the acid has a melting point above 50° C. It may likewise be desirable to carry out said mixing operation by introducing into the reaction zone first the hexachloropropene and then the organic acid, especially when use is made of organic acids having a melting point below 50° C or when use is made of organic acids having a melting point above 120° C.

The following equation represents the reaction of hexachloropropene with the organic acids in accordance with the practice of this invention:

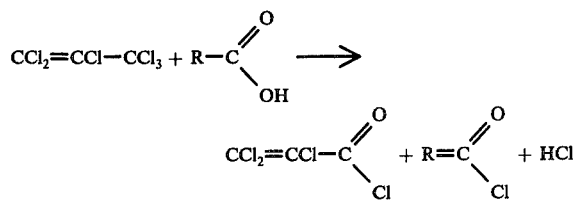

The reaction involves the formation of hydrochloric acid conjointly with that of trichloroacryloyl chloride and the chlorides of the acids. The course of the reaction can be followed very simply by analyzing the quantity of hydrochloric acid that is formed. Among the organic acid chlorides capable of being obtained simultaneously with the trichloroacryloyl chloride, in accordance with the practice of this invention, reference can be made particularly to monochloroacetyl chloride, trichloroacetyl chloride, propionyl chloride, butyryl chloride, caproyl chloride, capryloyl chloride, lauroyl chloride, benzoyl chloride, p-chlorobenzoyl chloride and anisoyl chloride.

For carrying out the process of this invention, it is advantageous to make use of stoichiometric quantities of hexachloropropene and organic acids and, when used, 0.01% to 10% by weight, and preferably 0.1% to 1% by weight catalyst. It is often times disirable to make use of a slight excess of hexachloropropene which may function in the manner of a solvent for the organic acids.

A first variant for carrying out the process of this invention and which is applicable in the event that the acid chlorides obtained have a volatility differing considerably from that of trichloroacryloyd chloride consists in collecting by distilling off the more volatile chloride as it is formed.

A second variant of carrying out the process of this invention consists in continuously introducing the reactants and continuously removing trichloroacryloyl chloride and the acid chlorides obtained. In accordance with this variation, the recovery of the chlorides, that is the recovery of trichloroacryloyl chloride and the acid chlorides, can be accomplished either by continuously removing said chlorides by decantation, followed by distillation in a connecting apparatus, or by continuously distilling the more volatile chloride under slight vacuum and continuously removing the less volatile chloride.

The invention is believed also to reside in the organic acid chlorides and trichloroacryloyl chloride prepared by the process of this invention and having the general formula:

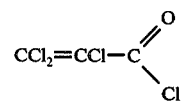

The following examples are given by way of illustration, but not by way of limitation, on the scope of the invention:

EXAMPLE 1

In a glass flask equipped with a stirrer and a reflux condenser, the following materials are introduced and heated to 120° C for 18 hours:

249 g hexachloropropene 94.5 g monochloroacetic acid
1 g zinc chloride
By distillation there is recovered:
93.5 g monochloroacetyl chloride, which corresponds to a 82.6% yield, based on the monochloroacetic acid used; and
147 g trichloroacryloyl chloride, which corresponds to a 76% yield based upon the hexachloropropene used.

EXAMPLE 2

Using the apparatus described in Example 1, the following mixture of materials is heated to 150° C for 4 hours:
249 g hexachloropropene
94.5 g monochloroacetic acid
1 g zinc chloride
By distillation there is recovered:
98.7 g monochloroacetyl chloride, which corresponds to a 87.4% yield, based upon the monochloroacetic acid used; and
176 g trichloroacryloyl chloride, which corresponds to a 90.8% yield based on the hexachloropropene used.

EXAMPLE 3

In the apparatus described in Example 1, there is heated to 150° C for 4 hours:
249 g hexachloropropene
163.5 g trichloroacetic acid
1 g zinc chloride
By distillation there is recovered:
150 g trichloroacetyl chloride, which corresponds to a 82.3% yield, based upon the trichloroacetic acid used; and
142 g trichloroacryloyl chloride, which corresponds to a 73.2% yield, based upon the hexachloropropene used.

EXAMPLE 4

In the apparatus described in Example 1, there is heated to 150° C for 6 hours:
249 g hexachloropropene
122 g benzoic acid
1 g zinc chloride
By distillation there is recovered:
120 g benzoyl chloride, which corresponds to a 85.4% yield, based upon the benzoic acid used; and
128 g trichloroacryloyl chloride, which corresponds to a 66.2% yield, based upon the hexachloropropene used.

EXAMPLE 5

This example relates to the simultaneous preparation of propionyl chloride and trichloroacryloyl chloride wherein the propionyl chloride formed is collected by distillation as it is formed.

The apparatus used consists of a glass flask of 1000 cm³ capacity equipped with a stirring device, a thermometer well, and a column having a diameter of 30 mm and a length of 400 mm packed with glass helices of 5 mm. On top of this column there is mounted a reflux condenser while the condensate, by means of a time switch, is either returned to the head of the column or delivered to a glass receiver. A column for washing with water is provided for the recovery of the hydrochloric acid formed and the hydrochloric acid is analyzed as a function of the time for determining the course of the reaction.

Into the described flask, there is introduced:
850 g hexachloropropene (3.42 moles)
222 g propionic acid (3 moles)
1 g zinc chloride The reaction mixture is heated to 150° C. The propionyl chloride formed is withdrawn by distillation after the temperature at the head of the column reaches 80° C. This temperature is reached after 1½ hours of heating.

During the following 2½ hours, there is recovered 225 g propionyl chloride.

Distillation of the composition remaining in the flask at the end of the the reaction yields:
23 g propionyl chloride, which corresponds to a yield of 89.2%, taking into account the product recovered during the operation;
45 g hexachloropropene; and
476 g trichloroacryloyo chloride, which corresponds to a yield of 75.8%, taking into account the 45 g of hexachloropropene which is not reacted.

I will be understood that changes may be made in the details of formulation and operation without departing from the spirit of the invention, especially as defined in the following claims.

I claim:
1. A process for the simultaneous preparation of organic acid chlorides and trichloroacryloyl chloride comprising the steps of contacting hexachloropropene and an organic acid having the formula

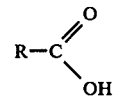

in which R is selected from the group consisting of alkyl, chloroalkyl, alkenyl, phenyl, chlorophenyl, methoxyphenyl and cycloalkyl, heating the mixture to a temperature within the range of 50° to 220° C, and separating the trichloroalkylolyl chloride and the organic acid chlorides produced.

2. The process as claimed in claim 1 in which the reaction is carried out in the presence of a catalyst.

3. The process as claimed in claim 2 in which the catalyst is selected from the group consisting of zinc chloride, ferric chloride and iodine.

4. The process as claimed in claim 2 in which the catalyst is present in an amount within the range of 0.1% to 10% by weight of the reaction mixture.

5. The process as claimed in claim 2 in which the catalyst is present in an amount within the range of 0.1% to 1% by weight of the reaction mixture.

6. The process as claimed in claim 1 in which the reaction is carried out at a temperature within the range of 120° to 180° C.

7. The process as claimed in claim 1 in which the reaction products are separated by distillation.

8. The process as claimed in claim 1 which includes the step of separating the most volatile chloride amongst the acid chlorides and trichloroacryloyl chloride that are formed.

9. The process as claimed in claim 1 in which the addition of the reactants and removal of the reaction product is carried out as a continuous operation.

10. The process as claimed in claim 1 in which the hexachloropropene and organic acids are combined for reaction in stoichiometric amounts.

11. The process as claimed in claim 1 in which the hexachloropropene is added for reaction with the organic acid in an amount ranging from the stoichiometric amount to a slight excess which can function as a solvent for the organic acid.

12. The process as claimed in claim 1 in which the organic acid component is selected from the group consisting of butyryl chloride, caproyl chloride, capryloyl chloride, lauroyl chloride, benzoyl chloride, p-chlorobenzoyl chloride and anisoyl chloride.

13. A process for the simultaneous preparation of organic acid chlorides and trichloroacryloyl chloride comprising the steps of contacting hexachloropropene and an organic acid having the formula

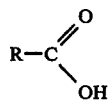

in which R is selected from the group consisting of alkyl, chloroalkyl, alkenyl, phenyl, chlorophenyl, methoxyphenyl and cycloalkyl, with the hexachloropropene being employed in substantially stoichiometric proportions with the organic acid, heating the resulting mixture in the presence of a catalyst selected from the group consisting of zinc chloride, ferric chloride and iodine to a temperature within the range of 50° to 220° C, and separating the trichloroalkylolyl chloride and the organic acid chlorides produced.

14. A process as claimed in claim 13 wherein the catalyst is present in an amount within the range of 0.1% to 10% by weight of the reaction mixture.

15. A process as claimed in claim 13 in which the organic acid is selected from the group consisting of butyric acid, capric acid, caprylic acid, lauric acid, benzoic acid, parachlorobenzoic acid and anisic acid.

16. A process for the simultaneous preparation of organic acid chlorides and trichloroacryloyl chloride comprising the steps of contacting hexachloropropene and an organic acid having the formula

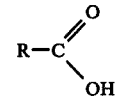

wherein R is selected from the group consisting of chloromethyl, trichloromethyl, ethyl, propyl, nonyl, octyl, undecyl, phenyl, chlorophenyl and methoxyphenyl, with the hexachloropropene being employed in substantially stoichiometric proportions with the organic acid, heating the resulting mixture in the presence of a catalyst selected from the group consisting of zinc chloride, ferric chloride and iodine to a temperature within the range of 50° to 220° C, and separating the trichloroalkylolyl chloride and the organic acid chlorides produced.

17. A process as claimed in claim 16 wherein the catalyst is present in an amount within the range of 0.1 to 10% by weight of the reaction mixture.

* * * * *